US009522395B2

United States Patent
Lind et al.

(10) Patent No.: US 9,522,395 B2
(45) Date of Patent: Dec. 20, 2016

(54) PIPETTE WITH A TRACKING SYSTEM

(71) Applicant: Thermo Fisher Scientific Oy, Vantaa (FI)

(72) Inventors: Mikael Lind, Helsinki (FI); Juha Telimaa, Jarvenpaa (FI)

(73) Assignee: Thermo Fisher Scientific Oy, Vantaa (FI)

( * ) Notice: Subject to any disclaimer, the term of this patent is extended or adjusted under 35 U.S.C. 154(b) by 184 days.

(21) Appl. No.: 14/377,308

(22) PCT Filed: Feb. 13, 2013

(86) PCT No.: PCT/FI2013/050165
§ 371 (c)(1),
(2) Date: Aug. 7, 2014

(87) PCT Pub. No.: WO2013/121109
PCT Pub. Date: Aug. 22, 2013

(65) Prior Publication Data
US 2015/0000429 A1    Jan. 1, 2015

(30) Foreign Application Priority Data
Feb. 13, 2012   (FI) .................................. 20125149

(51) Int. Cl.
*B01L 3/02*   (2006.01)

(52) U.S. Cl.
CPC .............. *B01L 3/021* (2013.01); *B01L 3/0237* (2013.01); *B01L 3/0286* (2013.01);
(Continued)

(58) Field of Classification Search
CPC ........ B01L 3/021; B01L 3/0237; B01L 3/0286
(Continued)

(56) References Cited

U.S. PATENT DOCUMENTS

2002/0095998 A1   7/2002   Kriz et al.
2004/0008191 A1   1/2004   Poupyrev et al.
(Continued)

FOREIGN PATENT DOCUMENTS

DE      602005004463 T2   1/2009
EP      0112887 B1        2/1986
(Continued)

OTHER PUBLICATIONS

Gilson SAS, Authors: Patrick Haddad and Jerome Deve, Assays Under Control With the Programmable Pipetman Concept, Jan. 31, 2007, XP055065438, retrieved from the Internet: URL:http://www.gilson.com/Resources/Assays under control.pdf, retrieved on Jun. 5, 2013, col. 4 (2 pages).

(Continued)

*Primary Examiner* — Benjamin Schmitt
(74) *Attorney, Agent, or Firm* — Wood Herron & Evans LLP

(57) ABSTRACT

A pipette is described which includes a piston for aspirating liquid into and dispensing out of a container in the pipette. The pipette is provided with at least one tracking element which is able to count the magnitude of some variable or variables relating to the amount of use of the pipette, at least one operating device for creating a limit magnitude for each variable, and for giving information when the limit value is exceeded. Thus, the user may, for instance, be warned when he may be exposed to high workload stress possibly causing injuries.

8 Claims, 5 Drawing Sheets

(52) U.S. Cl.
CPC ... *B01L 2200/143* (2013.01); *B01L 2300/024* (2013.01); *B01L 2300/027* (2013.01)

(58) Field of Classification Search
USPC .......................... 73/864.01, 864.13, 864.16
See application file for complete search history.

(56) References Cited

U.S. PATENT DOCUMENTS

| | | |
|---|---|---|
| 2005/0118069 A1 | 6/2005 | Solotareff et al. |
| 2006/0197753 A1 | 9/2006 | Hotelling |
| 2009/0000350 A1 | 1/2009 | Magnussen et al. |
| 2009/0071266 A1 | 3/2009 | Nelson et al. |
| 2009/0216465 A1* | 8/2009 | Millet ................... B01L 3/0217 702/50 |
| 2011/0034248 A1* | 2/2011 | Grever ................... A63F 13/06 463/36 |
| 2011/0072915 A1 | 3/2011 | Molitor et al. |
| 2011/0109563 A1 | 5/2011 | Liu |

FOREIGN PATENT DOCUMENTS

| | | |
|---|---|---|
| EP | 2256611 A2 | 12/2010 |
| TW | 201117070 A1 | 5/2011 |
| WO | 2005079989 A1 | 9/2005 |
| WO | 2012045415 A1 | 4/2012 |
| WO | 2012045417 A2 | 4/2012 |

OTHER PUBLICATIONS

Espacenet, English Machine Translation of Abstract, DE602005004463T2, published Jan. 15, 2009, retrieved from http://worldwide.espacenet.com on Jul. 17, 2014 (2 pages).
National Board of Patents and Registration of Finland, Search Report, Patent Application No. 20125149, mailed Nov. 14, 2012 (2 pages).
Gilson, Inc., Pipetman m—User's Guide, Aug. 31, 2010, XP055065435, retrieved from the Internet: URL:http://www.biolab.dk/uploads/pdf/Manualer/MLH/Bruger Manual for Gilson Pipetman M (Single).pdf, retrieved on Jun. 5, 2013 (32 pages).
EPODOC/EPO, English Machine Translation of Abstract, Taiwan Application No. 201117070A, published May 16, 2011, retrieved on Nov. 12, 2012 (1 page).
European Patent Office, International Search Report and Written Opinion of the International Searching Authority, International Application No. PCT/FI2013/050165, mailed Jun. 21, 2013 (11 pages).
State Intellectual Property Office of People's Republic of China, Office Action, Application No. 201380009064.1, Issued Apr. 5, 2016 (16 pages).

* cited by examiner

PIPETTE WITH A TRACKING SYSTEM

CROSS-REFERENCE TO RELATED APPLICATION

This application is a submission under 35 U.S.C. §371 of International Application No. PCT/FI2013/050165, filed Feb. 13, 2013, which claims priority to Finnish Application No. 20125149, filed Feb. 13, 2012, the disclosures of which are hereby expressly incorporated by reference herein in their entireties.

FIELD OF THE INVENTION

The present invention relates to liquid handling with hand-held pipettes and, more particularly, to the ergonomics of pipetting.

BACKGROUND OF THE INVENTION

Pipettes used for liquid dosage in laboratories comprise a piston movable in a cylinder for aspiration of liquid into a pipette tip connected with the cylinder. Such pipettes comprise an elongated handle held by palm grip. The volume is usually adjustable. Typically, there is also a mechanism for removing a used tip from the pipette. There are also multichannel pipettes comprising eight channels in a row. In manual pipettes, all the operations are carried out by hand force. The piston in almost all manual pipettes is moved by pushing with thumb a spring-loaded rod placed at the upper end of the pipette. Volume is usually set by rotating the knob. The tip is removed by pushing a spring-loaded push button at the side of the handle. There are also electronic pipettes in which the piston is actuated by means of an electric motor. The tip removal mechanism is still often manual, but there are also electronic pipettes in which also the tip removal mechanism is electrically driven. There may also be manual pipettes operated by hand force but comprising an electronic display.

Manual pipettes are described in European Patent Application No. EP 112 887 and electronic pipettes are described in European Patent Application No. EP 1 725 333.

An example of an electronic pipette is Finnpipette® Novus Electronic Pipette (Thermo Fisher Scientific Oy, Finland). This pipette contains also a counter which counts the total number of pipettings after the latest calibration. The user may go and check that number and consider whether recalibration is appropriate. After the recalibration, the counter is automatically reset.

Ergonomics is an important factor in pipetting. A typical user in a laboratory may have to make hundreds of repetitive pipetting series during a working day. The forces needed to move the piston and tip remover may be quite big especially in multichannel pipettes. The distance that the piston rod must be moved may be quite long in relation to the anatomy of a user's hand. In electric pipettes, the piston is not moved by hand force, but instead by operating a switch. The weight of an electric pipette is, however, usually bigger. Pipetting needs also often very accurate movements when liquid is taken from and dispensed into small vessels. This causes extra workload.

SUMMARY OF THE INVENTION

A pipette in accordance with one embodiment of the present invention comprises at least one tracking element which is able to count the magnitude of some variable or variables relating to the amount of use of the pipette. When the magnitude exceeds a certain limit value, the user is informed. Thus, the user may, for instance, be warned when he may be exposed to high workload stress possibly causing injuries. Variables that can be tracked may be, for example, the number of pipettings, the number of operations by a certain finger, the number of tip attachments or removals, or the time of operation.

BRIEF DESCRIPTION OF THE DRAWINGS

The accompanying drawings pertain to the written description of the present invention and relate to the following detailed description of the present invention. In the drawings.

DETAILED DESCRIPTION OF THE INVENTION

Figure 1:
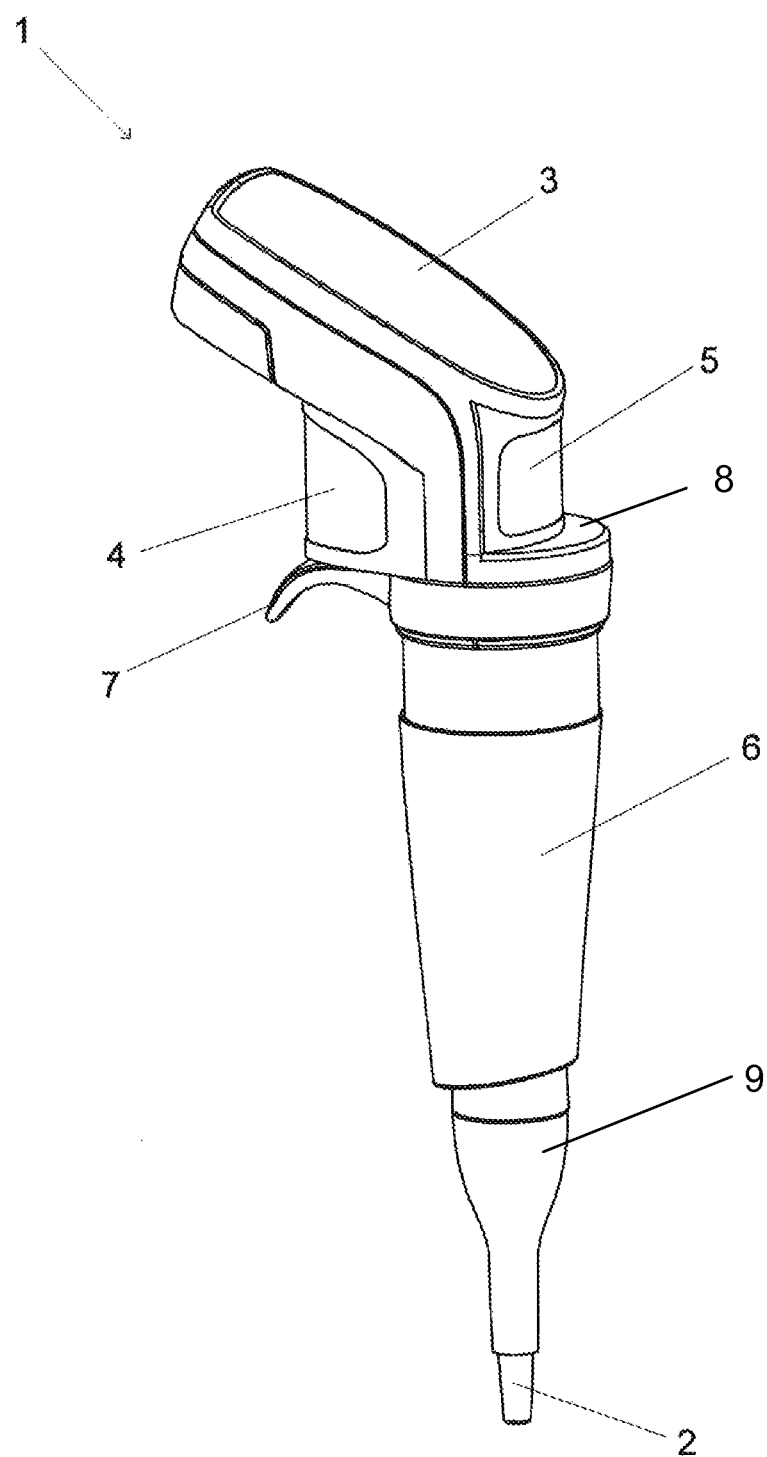
FIG. 1 shows a general view of a pipette of the present invention.

The pipette in accordance with one embodiment of the present invention comprises a barrel and a piston moveable in the barrel for liquid aspiration and dispensing. At the lower end of the barrel, there is usually a pipette tip into which the liquid is aspirated. In manual pipettes, the piston is moved by hand force, and in motor driven pipettes, by a motor. In manual pipettes, the piston is usually spring-loaded so that the piston is moved downwards by pressing it downwards, usually by thumb, against the spring force and then let to move upwards by the spring. The piston stroke can usually be changed so that the volume of the aspirated liquid can be adjusted. Volume is usually adjusted by rotating the rod of the piston. Typically, there is also a mechanism for removing used tips from the pipette. The mechanism usually comprises a spring-loaded remover so that the tips are removed by pressing the remover downwards. New tips are usually attached by pushing the lower end of the barrel tightly into the tip. There are also multichannel pipettes comprising several barrels, usually in a row. Also, in motor driven pipettes, the tip removal mechanism is often manual. In motor driven pipettes, there is usually an electronic display on which information of pipetting is shown. The operations are controlled by suitable operation keys. There may be also such pipettes which are operated by hand force but in which there is an electronic display.

The pipette, in accordance with one embodiment of the present invention, comprises at least one tracking element which is able to count the magnitude of some variable or variables relating to the amount of use of the pipette. Variables that may be counted are, for example, the number of pipettings, the number of liquid aspirations or dispensations, the number of operations by of certain finger, operating time, the number of tip attachments or removals, the duration of pressing actions, and the force used for a pressing. In mechanical pipettes, the tracking elements may also measure the physical lengths of pressing actions. There are suitable tracking elements connected to desired mechanisms or to an electronic control system. The number of some operations may also be estimated on the basis of the number of some other operations, for example, the number of tip removals may be estimated on the basis of liquid dispensations. The system may also track the combined magnitude of some variables.

There is also a suitable monitoring system, which, when the magnitude, especially calculated per a desired time interval, of some variable or combination of variables exceeds a certain predetermined threshold value, informs the user. This is preferably done by a suitable signal on a display or by a sound signal. Thus, the user may, for example, be warned when he may be exposed to a high workload stress which may cause injuries. The system may also suggest using different fingers for the functions used, or changing the places of functions, for example, changing functions between buttons or functions set to certain touch sites on a touch screen when touch screens are used. The monitoring system may be such that also some physical properties, for example, the weight, of the pipette can be input. Thus, the same monitoring program can be used in different types of pipettes (e.g., multichannel pipettes vs. single channel pipettes) or in similar type pipettes. The system may also give a pre-warning when the magnitude limit is approached.

The system is preferably such that the user can change the limits according to his personal needs. Limit values for different users may also be stored in the system.

According to one embodiment, statistics about the operation of the pipette is created. The results can be shown also graphically, for example, the number of a certain operation or given alarms per a desired time interval may be shown.

The ergonomic workload of different modes of use may also be compared and reported by the system. Thus, the user can optimize his working methods so that exposure to stress is minimized.

Additionally, the user may be informed about possible need of service. To keep the pipette operating as well as possible, it may be necessary to regularly check the accuracy of operations and recalibrate the volume setting or change worn parts. Also, the battery may be monitored, for example, the number of loadings may be counted and warnings (e.g., light on display, or notifications in reports) given when change of battery is needed.

According to one embodiment of the present invention, the pipette comprises at least one touch screen so that operation keys are positioned as touch sites on the screen. Also, information about operations can be shown on the screen. It is also possible to change the locations of the touch sites to be suitable for different users or for balancing the stress between different fingers.

If several persons use the same pipette, it is possible to arrange the monitoring system to track the use by different persons separately.

FIG. 1 shows an electronic pipette 1, which comprises a piston movable in a cylinder by an electric motor. A pipette tip (not shown) is attached to the lower end 2 extending from the cylinder. There are three touch screens 3, 4, 5 for operating the pipette. The pipette is gripped with hand from the handle portion 6, which handle portion also comprises at its upper end a finger support 7. The finger support is rotatable so that it can be positioned best suitable to the actual user. The touch screen 4 can be operated with the index finger of the gripping hand and the touch screens 3 and 5 can be operated with the thumb or by fingers of the other hand. There is also a tip removal mechanism comprising a tip ejector button 8. When the button is pressed, the sliding sleeve 9 pushes the tip loose.

The term touch screen here means an electronic visual display that displays information and that can detect the presence and location of a touch within the display area.

The touch screens may be used as modifiable function keys or buttons by which the pipetting operations are controlled. The touch screens may be equipped with pre-programmed icons for different operations, whereby the icons define the active pressing areas of the touch screen for activating related. These icons may be moved to different places on the touch screen or on different touch screens. The size of the icons, or the active area of the touch screen for receiving a touch to activate selected operation, may also be adjustable. Some areas of the touch screens or whole touch screen may also be adjusted to be inactive, so they may be used as a support surfaces when operating the pipette.

The touch screens may also be equipped with sliding functions, whereby, for example, the pipetting motion can be carried out by moving finger along the surface of the touch screen, which corresponds to a similar type of motion in manual pipettes. In this sliding function, the piston follows the movement of the finger in real time. Alternatively, this sliding function can be used to activate mixing function, for example.

It is also possible to change locations of areas registering pressing or touching for operating to be suitable for different users and for different hands, thereby minimizing the stress caused to the hand when operating. It is also possible to easily switch the locations of the pressing or touching areas, for example, for different fingers, during the use, which makes it possible to further minimize the stresses caused by pipetting.

The touch screen 3 is disposed at the top of the pipette, in a position upwardly oblique away from the push-button 6 of the tip removal sleeve on the upper surface of a projection. A power source is provided within the projection. This touch screen shows necessary information about the settings used each time, such as, for example, the pipette volume and function in use and the current function step. The display also shows, depending on the situation, different menus in which the settings can be changed.

Figure 2:
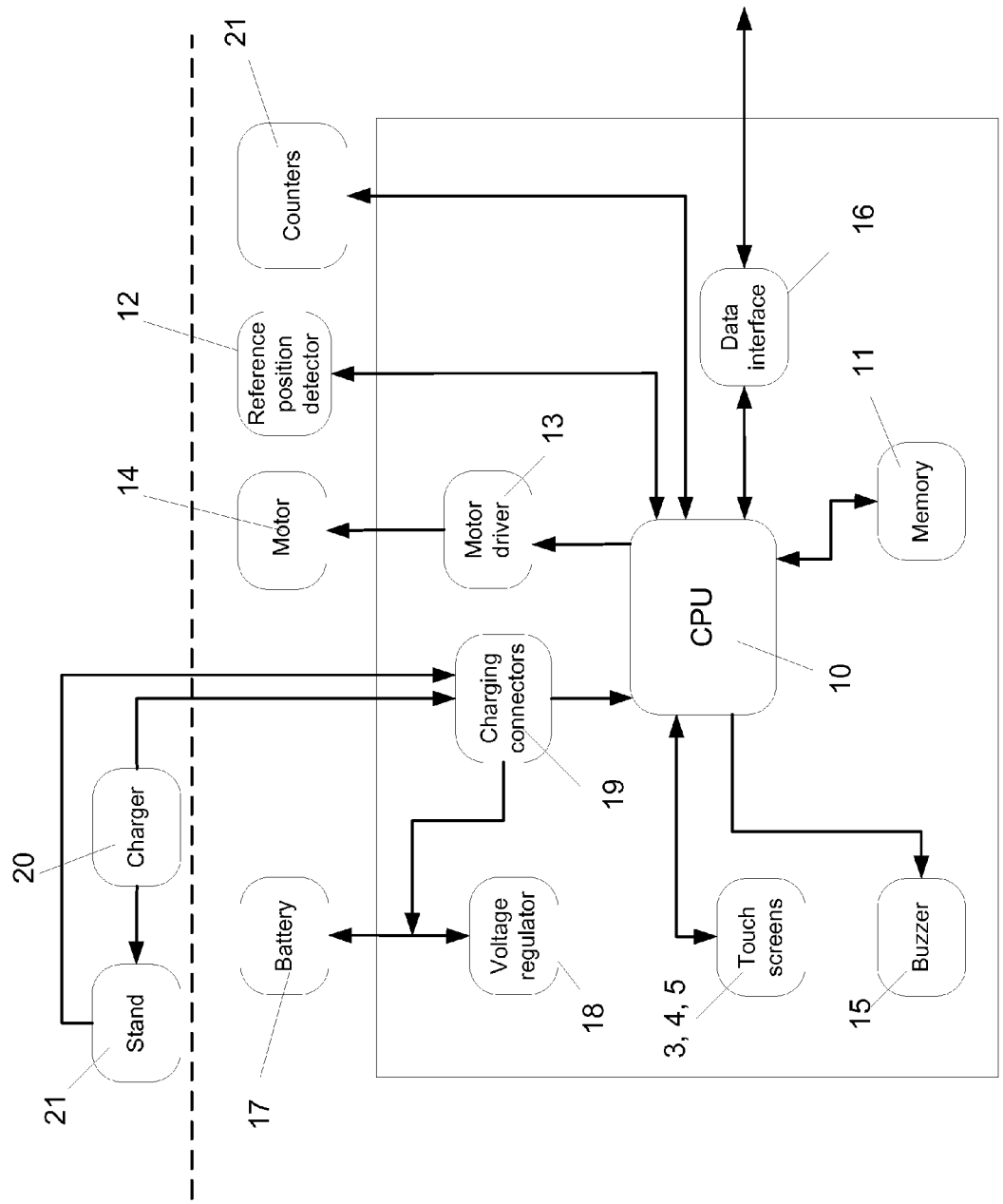
FIG. 2 is a schematic view of the operation of the pipette.

FIG. 2 shows the pipette functions as a chart. The core of the control system is a central processing unit (CPU) 10 connected with a memory 11. The CPU is used by means of keys shown on the touch screens 3, 4, 5. The CPU is informed of the piston position by a position sensor 12. The CPU gives the commands needed for actuating the piston to a driver 13, which controls a step motor 14. The functions are indicated on the screen 3. Some functions are indicated with acoustic signals by means of a buzzer 15. In addition, the CPU is connected to a serial interface 16 allowing data input into or output. A chargeable battery 17 acts as a voltage source. The battery is connected to a voltage regulator 18. The battery is charged over terminals 19 using a charger 20 in a stand 21. The charging is also controlled by the CPU.

There are also counters 21 connected with the CPU. These counters may separately count, for example, the number of pipettings, the number of liquid aspirations or dispensations, the number of uses with index finger, the number of uses with thumb, operating time, the number of tip ejections, the number of tip attachments, the duration of pressing actions, and the force used for pressings.

Figure 3:
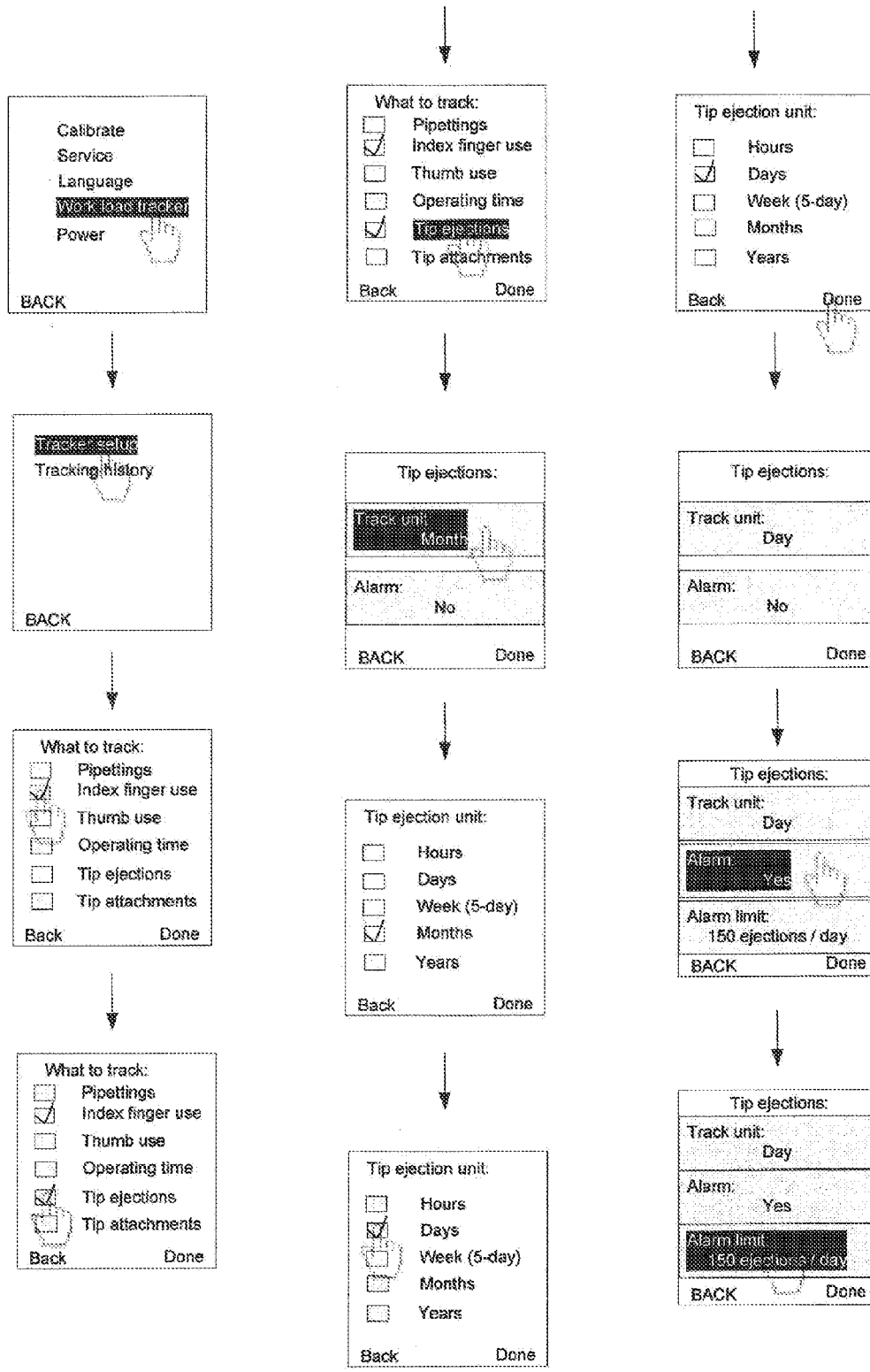
FIGS. 3(1), 3(2) and 3(3) show a schematic view of a series of some operations of the pipette.
Figure 3:
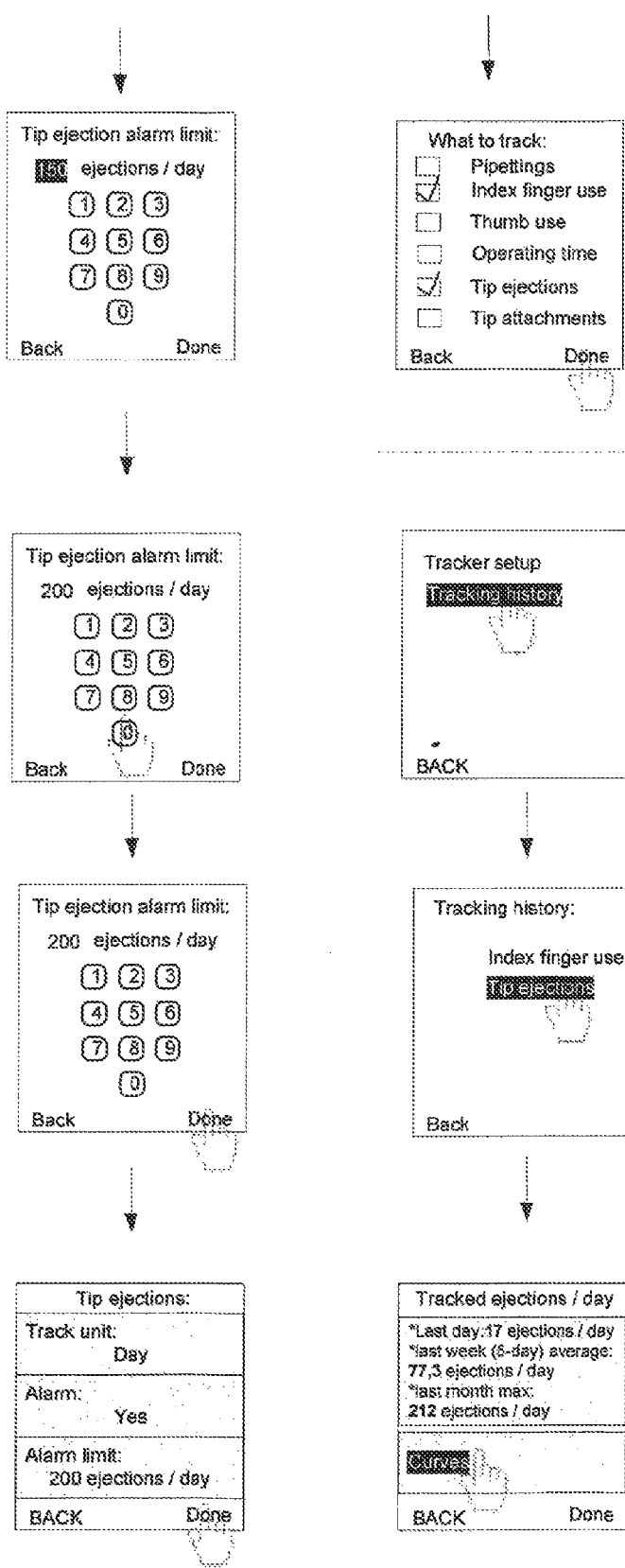
Figure 3:
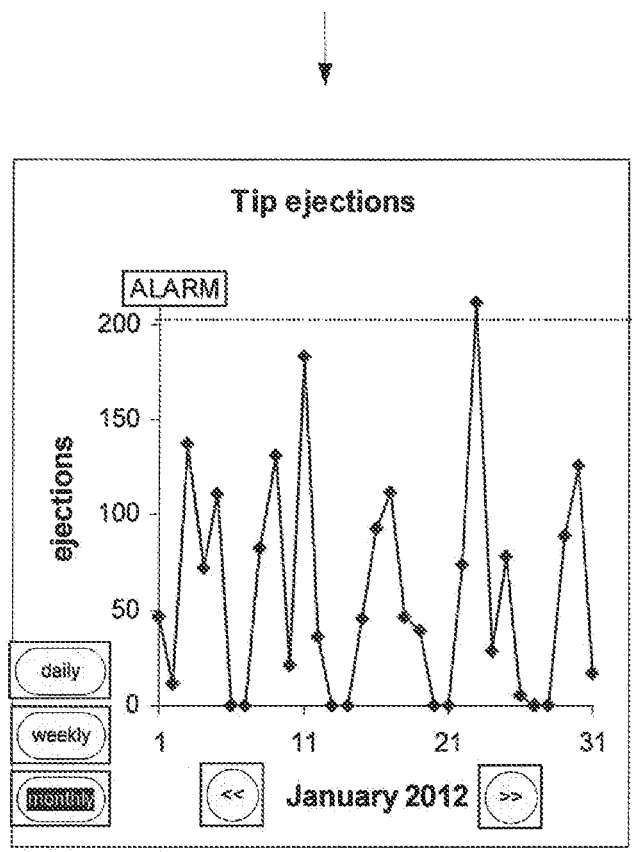

FIG. 3 shows one sequence for setting up a tracking system and studying its history. The pictures show a sequence of views on the touch screen 3. The steps selected in each phase are shown with the picture of hand.

The first phase opens up a menu from which "Work load tracker" is selected. It is then possible to select between "Tracker setup" and "Tracking history", and, when the first one is selected, a menu opens showing different variables which are possible to be tracked by the counters 21. First, the user selects "Index finger use" to be tracked and then "Tip ejections" by marking the boxes on the left side of the screen. Other variables that can be selected are "Pipettings", "Thumbuse", "Operating time", and "Tip attachments". When touching the text "Tip ejections", a new window opens. It can be seen that "Track unit" is now "Month" and that no "Alarm" has been set. This is changed by touching the box, and selecting "Days" from the opening menu. Now it is returned to the window in which "Alarm" is shown. When this box is touched, "No" changes to "Yes" and a new box "Alarm limit" appears showing that the present limit is 150 ejections/day. When the box is touched, a number keyboard opens up (first view of FIG. 3(2)), on which 150 is changed to 200. Now the changed tip ejection tracking mode is set, and it is shown on the screen. Also, the other selected variables to be tracked can be set in a corresponding way. If not changed, the previous (or default) settings remain valid.

When the amount of a selected variable exceeds the set limit, an alarm appears on the screening warning the user from possible stress risk.

Returning to the second view of FIG. 3(1), touching "Tracking history" opens up a window from which the history of the tracked variables can be studied. When "Tip ejections" is touched, a window opens up showing the history in text format. There is also a "Curves" box, through which the history data can be seen in graphical form (see view of FIG. 3(3)). Here, one can also select the time range from which the data is desired.

While the present invention has been illustrated by description of various embodiments and while those embodiments have been described in considerable detail, it is not the intention of Applicants to restrict or in any way limit the scope of the appended claims to such details. Additional advantages and modifications will readily appear to those skilled in the art. The present invention in its broader aspects is therefore not limited to the specific details and illustrative examples shown and described. Accordingly, departures may be made from such details without departing from the spirit or scope of Applicants' invention.

What is claimed is:

1. A pipette comprising a piston movable in a barrel and used for aspirating liquid into and dispensing out of a container in the pipette, wherein the pipette comprises:
   at least one tracking element which is able to count the magnitude of some variable or variables relating to the amount of use of the pipette and operating time of the pipette,
   at least one operating device for creating a limit magnitude for each variable and for a time interval, and for giving information when the limit magnitude is exceeded within the time interval,
   wherein a weight of the pipette is taken into account in creating the limit magnitude.

2. The pipette according to claim 1, wherein the at least one operating device comprises a touch screen.

3. The pipette according to claim 1, wherein the at least one operating device comprises a plurality of touch screens.

4. A method for controlling the use of a pipette, comprising:
   a piston movable in a barrel used for aspirating liquid into and dispensing out of a container in the pipette, and
   a control system controlling movement of the piston, wherein a magnitude of at least one variable relating to the amount of use of the pipette and operating time of the pipette are counted by a tracking element, a limit value for the magnitude and time interval are created into the control system, and if the magnitude of the variable exceeds the limit value within the time interval, information that the magnitude of the variable exceeds the limit value within the time interval is given,
   wherein a physical property of the pipette is put into the control system and the limit value is calculated so that the physical property is taken into account in calculating the limit value, the physical property comprising weight of the pipette.

5. The method according to claim 4, wherein the variable to be counted is the amount of use of a certain finger, and when the limit value is exceeded the user is suggested to change the use of fingers.

6. The method according to claim 5, wherein the control system comprises at least one touch screen with operating buttons the places of which on the screen can be changed, and wherein the user is suggested to change the places of buttons on the screen.

7. The method according to claim 4, wherein statistics are created and shown from the use history of the pipette.

8. The method according to claim 7, wherein the statistics are shown graphically.

* * * * *